United States Patent [19]
Helmchen et al.

[11] Patent Number: 5,990,320
[45] Date of Patent: Nov. 23, 1999

[54] OPTICALLY ACTIVE DIPHOSPHINE LIGANDS

[75] Inventors: Günther Helmchen, Heidelberg; Christoph Mürmann, Schifferstadt, both of Germany

[73] Assignee: BASF Aktiengesellschaft, Ludwigshafen, Germany

[21] Appl. No.: 09/097,864

[22] Filed: Jun. 16, 1998

[30] Foreign Application Priority Data

Jun. 18, 1997 [DE] Germany .................. 197 25 643

[51] Int. Cl.⁶ .................. C07F 9/655; C07F 5/02; C07F 15/00
[52] U.S. Cl. .................. 549/218; 549/206; 549/213; 502/207; 502/213
[58] Field of Search .................. 549/218, 206, 549/213

[56] References Cited

U.S. PATENT DOCUMENTS

| | | | |
|---|---|---|---|
| 4,187,241 | 2/1980 | Townsend et al. | 260/438 |
| 4,634,775 | 1/1987 | Beck et al. | 548/402 |
| 4,652,657 | 3/1987 | Broger et al. | 548/402 |
| 4,668,795 | 5/1987 | Andrade et al. | 548/412 |
| 5,177,220 | 1/1993 | Schaefer et al. | 549/314 |

FOREIGN PATENT DOCUMENTS

| | | |
|---|---|---|
| 151 282 | 8/1985 | European Pat. Off. . |
| 158 875 | 10/1985 | European Pat. Off. . |
| 184872 | 6/1986 | European Pat. Off. . |
| 185 882 | 7/1986 | European Pat. Off. . |
| 269 395 | 6/1988 | European Pat. Off. . |
| 271 311 | 6/1988 | European Pat. Off. . |
| 437 690 | 7/1991 | European Pat. Off. . |
| 614 901 | 9/1994 | European Pat. Off. . |
| 97/13763 | 4/1997 | WIPO . |

OTHER PUBLICATIONS

J. Am. Chem. Soc., vol. 106, 1984, 4653–5766, Tani et al.
Acc. Chem. Res. 1990, 23, 345–350, Noyori et al.
Asymmetric Synthesis vol. 5, Chiral Catalysis, 13–23.
Tetrahedron:Asymmetry, vol. 2, No. 7, pp. 569–592, 1991.
J. Am. Chem. Soc., vol. 1991,11, 8518–8519, Burk.
J. Am. Chem. Soc., 1996, 118, 5142–5143, Burk et al.
J. Am. Chem. Soc., 1995, 117, 9375–9376, Burk et al.
J. Am. Chem. Soc. 1993, 115, 10125–10138, Burk et al.
Tetrahedron vol. 43, No. 21, pp. 5055–5072, 1987, Hanessian et al.
Tetrahedron vol. 38, No. 15, 2377–2394, 1982, Cardellach et al.
Inorganic Chimica Acta, 73 (1983)275–279, Uson et al.
Jansen et al., *Tetrahedron: Asymmetry*, vol. 1, No. 10. pp. 719–720, 1990.

*Primary Examiner*—Amelia Owens
*Attorney, Agent, or Firm*—Keil & Weinkauf

[57] ABSTRACT

Optically active diphosphine ligands of the formula I,

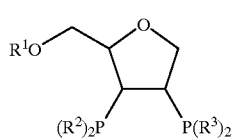

I where:
$R^1$ is hydrogen, $C_1$–$C_{10}$-acyl, $C_1$–$C_{10}$-alkyl, $C_2$–$C_{10}$-alkenyl, each of which may be linear or branched, aryl, arylalkyl, in which the ring systems may be substituted in each case,

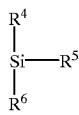

$R^2$, $R^3$ independently of one another are $C_1$–$C_{10}$-alkyl, which may be linear or branched, aryl, arylalkyl, in which the ring systems may be substituted in each case,
$R^4$, $R^5$, $R^6$ independently of one another are $C_1$–$C_{10}$-alkyl, which may be linear or branched, aryl, arylalkyl, in which the ring systems may be substituted in each case.

9 Claims, No Drawings

OPTICALLY ACTIVE DIPHOSPHINE LIGANDS

The present invention relates to optically active diphosphines, to a process for preparing optically active diphosphines and their transition metal complexes, and to the use of the metal complexes for enantioselective synthesis.

Enantioselective hydrogenation and isomerization with rhodium and ruthenium complexes is very important in the synthesis of optically active compounds [e.g. Tani et al., J. Am. Chem. Soc. 106 (1984) 5211; R. Noyori, Acc. Chem. Res. 23 (1990) 345]. However, the catalysts used for this purpose, which are usually prepared from an optically active diphosphine ligand and a rhodium or ruthenium compound, are very costly and can be obtained only by elaborate preparation processes.

Known methods for preparing optically active phosphines and diphosphines are all complicated and usually include an industrially elaborate and costly racemate resolution (e.g. EP-A-0 614 901; EP-A-0 271 311; H. B. Kagan, "Chiral Ligands for Asymmetric Catalysis" in Asymmetric Synthesis, Vol. 5 (1985), 13–23, EP-A- 0 151 282; EP-A-0 185 882; R. Noyori, Acc. Chem. Res. 23 (1990) 345; EP-A-0 269 395; M. J. Burk, Tetrahedron, Asymmetry, (1991) 569–592; J. Am. Chem. Soc. 113 (1991) 8518–19, ibid. 115 (1993) 10125–138, ibid. 117 (1995) 9375–76, ibid. 118 (1996) 5142). These disadvantages make industrial utilization of such catalysts at present difficult and uneconomic.

It is an object of the present invention to provide optically active diphosphines which are suitable as ligands for transition metal complex catalysts and whose preparation avoids the disadvantages indicated above.

We have found that this object is achieved by providing optically active diphosphines of the formula I

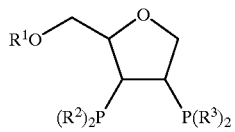

where:
$R^1$ is hydrogen, $C_1$–$C_{10}$-acyl, $C_1$–$C_{10}$-alkyl, $C_2$–$C_{10}$-alkenyl, each of which may be linear or branched, aryl, arylalkyl, in which the ring systems may be substituted in each case,

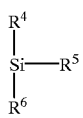

$R^2$, $R^3$ independently of one another are $C_1$–$C_{10}$-alkyl, which may be linear or branched, aryl, arylalkyl, in which the ring systems may be substituted in each case,
$R^4$, $R^5$, $R^6$ independently of one another are $C_1$–$C_{10}$-alkyl, which may be linear or branched, aryl, arylalkyl, in which the ring systems may be substituted in each case.

Acyl radicals for $R^1$ in the novel diphosphine ligands of the formula I are branched or unbranched, saturated or unsaturated, where appropriate polyunsaturated $C_1$–$C_{10}$-acyl chains, in particular formyl, acetyl, propionyl, n-butyryl, iso-butyryl and pivaloyl.

Alkyl radicals $R^1$ to $R^6$ which may be mentioned are branched or unbranched $C_1$–$C_{10}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl.

Alkenyl radicals $R^1$ which may be mentioned are branched or unbranched $C_2$–$C_{10}$-alkenyl chains, preferably vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Aryl for $R^1$ to $R^6$ means aromatic rings or ring systems having 6 to 18 carbon atoms in the ring system, for example phenyl or naphthyl, each of which may be substituted by one or more radicals such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals, in particular sulfo. Unsubstituted or substituted phenyl, methoxyphenyl and naphthyl are preferred.

Arylalkyl radicals which may be mentioned for $R^1$ to $R^6$ are branched or unbranched phenyl-$C_1$–$C_5$-alkyl or naphthyl-$C_1$–$C_5$-alkyl radicals such as phenylmethyl, phenylethyl, phenylpropyl, phenyl-1-methylethyl, phenylbutyl, phenyl-1-methylpropyl, phenyl-2-methylpropyl, phenyl-1,1-dimethylethyl, phenylpentyl, phenyl-1-methylbutyl, phenyl-2-methylbutyl, phenyl-3-methylbutyl, phenyl-2,2-dimethylpropyl, phenyl-1-ethylpropyl, naphthylmethyl, naphthylethyl, naphthylpropyl, naphthyl-1-methylethyl, naphthylbutyl, naphthyl-1-methylpropyl, naphthyl-2-methylpropyl, naphthyl-1,1-dimethylethyl, naphthylpentyl, naphthyl-1-methyl-butyl, naphthyl-2-methylbutyl, naphthyl-3-methylbutyl, naphthyl-2,2-dimethylpropyl, or naphthyl-1-ethylpropyl, and their isomeric or stereoisomeric forms. Substituted or unsubstituted phenyl or naphthyl radicals may be mentioned as aryl radicals.

Arylalkyl radicals for $R^1$ also mean $C(Ph)_3$ where the phenyl rings may be substituted by one or more radicals such as halogen, e.g. fluorine, chlorine or bromine, cyano, nitro, amino, $C_1$–$C_4$-alkyl-amino, $C_1$–$C_4$-dialkylamino, hydroxyl, $C_1$–$C_4$-alkyl, $C_1$–$C_4$-alkoxy or other radicals.

Particularly preferred optically active diphosphine ligands are those of the formula Ia,

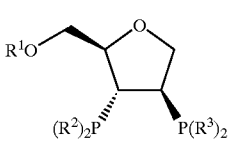

where $R^1$ is $C(CH_3)_3$, $C(Ph)_3$,

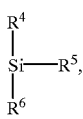

$R^2$, $R^3$ independently of one another are aryl, arylalkyl, in which the ring systems may be substituted in each case, $R^4$,$R^5$,$R^6$ independently of one another are $C_1$–$C_{10}$-alkyl, which may be linear or branched, aryl, arylalkyl, in which the ring systems may be substituted in each case.

The invention additionally relates to a process for preparing optically active diphosphine ligands of the formula I, which comprises a) reacting an optically active α,β-unsaturated lactone of the formula II

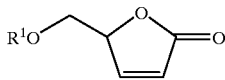

II as Michael acceptor with the anion of $HP(R^2)_2$ and then with $HalP(R^3)_2$, where $R^1$ to $R^3$ have the meanings stated in claim 1, and b) reducing the carbonyl functionality of the diphosphine-substituted lactone of the formula III

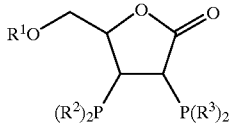

III to the methylene group.

The invention thus also relates to optically active diphosphine ligands of the formula III where the substituents have the meanings stated in claim 1.

The optically active α,β-unsaturated lactone II which acts as Michael acceptor can be prepared in a known manner either from D-ribono-1,4-lactone as disclosed in Tetrahedron 43 (21) (1987) 5055 or from glyceraldehyde as described in Tetrahedron 38 (15) (1982) 2377.

The anion $P(R^2)_2{}^\ominus$ can be generated from the corresponding phosphine [$HP(R^2)_2$] in the presence of a strong base. Strong bases which can be employed include organolithium compounds, for example butyllithium or lithium diisopropylamide (LDA), and alcoholates, in a manner known per se. A possible counterion (cation) is, besides sodium, potassium, magnesium and aluminum, preferably lithium.

Introduction of the second phosphine residue can take place using halodialkylphosphines or halodiarylphosphines, preferably halodiarylphosphines, in particular chlorodiphenylphosphine.

Solvents which can be employed for this reaction are all conventional inert solvents. Examples of preferred solvents are toluene, hexane, cyclohexane, THF, MTB and diethyl ether.

The reaction can be carried out at from $-100°$ C. to $+50°$ C., preferably from $-80°$ C. to $+30°$ C., with strict exclusion of oxygen.

Because the diphosphine-substituted lactones of the formula III which are formed are very sensitive to hydrolysis and oxidation, it is advantageous to convert them into the corresponding stable borane adducts by reaction with $BH_3$.

The lactones of the formula III or their borane adducts can be reduced to the corresponding cyclic ethers in a manner known per se (Organikum, 19th edition, Deutscher Verlag der Wissenschaften, 1993, 510–514) using complex metal hydrides such as $LiAlH_4$, $NaBH_4$ or DIBAH. The preferred reducing agent is diisobutylaluminum hydride (DIBAH) combined with silanes, e.g. $Et_3SiH$, $Ph_3SiH$ or $PhSiH_3$, and with $BF_3$ for subsequent reduction of the lactol.

Liberation of the optically active diphosphine ligands from their borane adducts can take place by treatment with basic reagents, preferably organic amines, in particular by treatment with diethylamine or triethylenediamine (1,4-diazabicyclo[2.2.2.]-octane, DABCO). This cleavage preferably takes place by brief heating of the borane adduct in the presence of the amine, followed by repeatedly evaporating off the volatile constituents.

The following reaction diagram shows a preferred process for preparing the novel diphosphines by way of example.

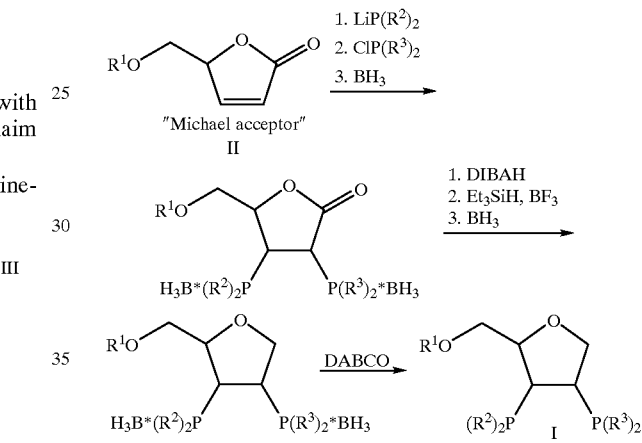

The novel optically active diphosphine ligands are outstandingly suitable for complexing transition metal compounds.

The invention therefore also relates to transition metal complexes of the formula IV, $$[M(L_n)(A)]^{p(+)} D^{q(-)} \qquad IV$$

where:

M is Co, Ir, Ni, Pd, Pt, Rh, Ru,

A is an optically active diphosphine ligand of the formula I, particularly preferably of the formula Ia L is an organic ligand, D is the equivalent of a non-coordinated anion, n is 1 or 2, p, q are 0 to 4.

M is preferably a metal from the group of Ru, Rh and Ir. D is preferably $CF_3COO^-$, $BF_4^-$, $SbF_6^-$, $SbCl_6^-$, $PF_6^-$, $(C_6H_5)_4B^-$.

L for the purpose of the present invention is an easily replaceable ligand such as olefins, for example ethylene, propylene, cyclooctene, 1,5-hexadiene or 1,5-cyclooctadiene.

The invention additionally relates to a process for preparing the abovementioned transition metal complexes, which comprises reacting an optically active diphosphine ligand of the formula I in a manner known per se with a transition metal compound $[ML_n]^{p(+)} D^{q(-)}$, where L is a replaceable ligand of the above-mentioned definition.

It is thus possible, for example, to synthesize from these novel phosphines in a known manner [e.g. Uson, Inorganic Chim. Acta 73 (1983) 275, EP-A-0 158 875, EP-A-0 437 690] catalytically active complexes by reaction with transition metal complexes which contain labile ligands, in particular with $[RuCl_2(COD)]_n$, $Rh(COD)_2BF_4$, $Rh(COD)_2ClO_4$, $[Ir(COD)Cl]_2$, p-cymene-ruthenium chloride dimer.

The transition metal complexes of the formula IV are suitable as catalysts for asymmetric reactions, in particular for the asymmetric hydrogenation of compounds with C—C, C—N and C—O multiple bonds, particular mention being made here of the hydrogenation of β-keto esters, allyl alcohols, enamides and dehydro amino acids. The transition metal complexes of the formula IV are likewise suitable for the asymmetric isomerization of allylamines to enamines and for asymmetric hydroformylation reactions.

The following examples explain the preparation of the novel optically active diphosphine ligands and their transition metal complexes, and the use of the metal complexes for enantioselective synthesis, in detail.

EXAMPLE 1

Preparation of the Diphenylphosphine-Borane Adduct of the Formula

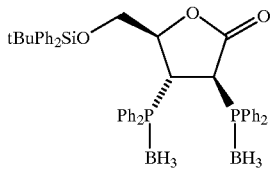

3.27 g (17.6 mmol) of diphenylphosphine were dissolved in 50 ml of THF and, at −78° C., deprotonated by 19.1 mmol of n-butyllithium. A solution of 5.543 g (15.7 mmol) of Michael acceptor of the formula II ($R^1$=tBuPh$_2$Si) in 50 ml of THF was cooled to −78° C. and added dropwise to the phosphine solution using a double-ended needle. After half an hour, 4.20 g (19.1 mmol) of chlorodiphenyl-phosphine, dissolved in 50 ml of THF were added. The reaction solution was allowed to reach room temperature overnight, and was again cooled to −78° C. before adding 45 ml of 1M borane solution in THF. After one hour, the solvent was evaporated off under medium vacuum, the residue was taken up in ethyl acetate, and the solution was washed with water. The product was obtained by flash chromatography on silica gel in a yield of 9.45 g (81%) in the form of a colorless amorphous solid.

Melting point: 133–134° C.

Optical rotation:

$[\alpha]^{20}_D=-57.1$, $[\alpha]^{20}_{578}=-59.9$, $[\alpha]^{20}_{546}=-69.1$, $[\alpha]^{20}_{436}=-127.4$, $[\alpha]^{20}_{365}=-222.5$; (c=1.14, CHCl$_3$).

$^1$H NMR (CDCl$_3$, 300.13 MHz): d (ppm)=0.3–1.6 (bs, 6 H, BH$_3$), 0.97 (s, 9 H, C(C$\underline{H}_3$)$_3$), 3.11 (dd, J$_{6,6'}$=10.9 Hz, J$_{5,6}$=7.0 Hz, 1 H, 6-H), 3.30 (dd, J$_{6,6'}$=10.7 Hz, J$_{5,6'}$=6.5 Hz, 1 H, 6'-H), 3.94 (ddd, $^2$J$_{3,P}$=20.2 Hz, $^3$J$_{3,P}$=10.5 Hz, J$_{3,4}$=3.4 Hz, 1 H, 3-H), 4.15 (m, 1 H, 4-H), 4.64 (m, 1 H, 5-H), 7.22–7.88 (sh, 30 H, Ar—H).

$^{13}$C NMR (CDCl$_3$, 75.47 MHz): d (ppm)=19.2 (s, $\underline{C}$(CH$_3$)$_3$), 26.9 (q, CH$_3$), 34.4 (d, $^1$J$_{C,P}$=38.4 Hz, C-4), 40.8 (d, $^1$J$_{C,P}$=26.0 Hz, C-3), 65.3 (t, $\underline{C}$H$_2$OSi), 79.1 (d, C-5), 127.7, 127.8, 128.7, 128.8, 128.9, 129.1, 129.1, 129.2, 129.8, 129.9, 131.6, 132.1, 132.3, 132.4, 132.5, 132.9, 133.1, 133.3, 133.5, 133.6, 134.1, 134.2, 135.4 (Ar), 171.0 (s, C=O).

$^{31}$P NMR (CDCl$_3$, 81.015 MHz): d (ppm)=23.9 (m, P-BH$_3$)

EXAMPLE 2

Reduction of the Lactone to the Ether of the Formula

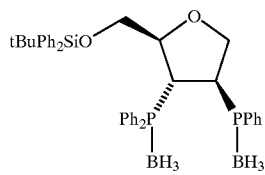

2.1 g (2.74 mmol) of the diphosphine obtained in Example 1 were dissolved in 20 ml of toluene and cooled to −78° C. and 2.9 ml of 1M DIBAH solution were added dropwise. After an aqueous workup, the residue was dissolved in 20 ml of dichloromethane, the solution was cooled to −78° C., and 666 mg (5.73 mmol) of triethylsilane and 412.3 mg (2.91 mmol) of boron trifluoride diethyl etherate were added. The mixture was allowed to reach room temperature overnight, and three more drops of boron trifluoride diethyl etherate were added to complete the reaction. After addition of 6 ml of 1M-BH$_3$ solution in THF, workup was carried out without protective gas to result in 1.3743 g (68%) of amorphous powder.

Optical rotation:

$[\alpha]^{20}_D=-25.0$, $[\alpha]^{20}_{578}=-26.2$, $[\alpha]^{20}_{546}=-30.2$, $[\alpha]^{20}_{436}=-54.4$, $[\alpha]^{20}_{365}=-91.6$, (c=1.41, CHCl$_3$).

$^1$H NMR (CDCl$_3$, 300.13 MHz): d (ppm)=0.3–1.6 (bs, 6 H, BH$_3$), 0.99 (S, 9 H, C(C$\underline{H}_3$)$_3$), 3.19 (dd, J$_{6,6'}$=10.8 Hz, J$_{2,6'}$=3.8 Hz, 1 H, 6-H), 3.54 (m, 1 H, 6'-H), 3.55 (m, 1 H, 3-H), 3.77 (ddd, J$_{5,P}$=16.3 Hz, J$_{5,5'}$=8.4 Hz, J$_{5,4}$=5.1 Hz, 1 H, 5-H), 3.87 (m, 1 H, 4-H), 3.93 (ddd, J$_{5',4'}$=15.7 Hz, J$_{5',P}$=10.6 Hz, J$_{5',5}$=7.8 Hz, 1 H, 5'-H), 4.31 (m, J$_{2,P}$=14.7 Hz, 1 H, 2-H), 7.22–7.88 (sh, 30 H, Ar—H).

$^{13}$C NMR (CDCl$_3$, 75.47 MHz): d (ppm)=19.0 (s, $\underline{C}$(CH$_3$)$_3$), 26.6 (q, CH$_3$), 35.8 (d, J$_{P,C}$=40.1 Hz, C-3), 35.9 (d, J$_{P,C}$=40.0 Hz, C-4), 64.4 (t, J$_{P,C}$=5.4 Hz, $\underline{C}$H$_2$OSi), 70.3 (t, J$_{P,C}$=J$_{P',C}$=4.2 Hz, C-5), 83.1 (d, J$_{P,C}$=J$_{P',C}$=4.6 Hz, C-2), 127.3–135.4 (Ar—C).

$^{31}$P NMR (CDCl$_3$, 81.015 MHz): d (ppm)=19.6 (m, P—BH$_3$).

EXAMPLE 3

Liberation of the Phosphines from their Borane Adducts

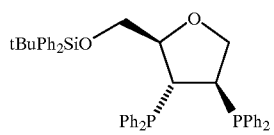

1 mmol of borane adduct from Example 2 was mixed with 0.5 ml of diethylamine and refluxed for 30 min. The volatile constituents were then removed twice under high vacuum. The free phosphines were obtained as air-sensitive white powders.

EXAMPLE 4

Preparation of the Rhodium Complex and Asymmetric Hydrogenation of α-Acetamidocinnamic Acid 110 μmol of the optically active diphenylphosphine ligand of Example 3 were dissolved in 5 ml of THF and, after addition of 100 μmol of $Rh(COD)_2BF_4$, stirred at RT for 20 min. 100 mmol of α-acetamidocinnamic acid and 250 ml of THF were added to the clear yellow solution. This solution was hydrogenated under 20 bar of hydrogen at 30° C. The reaction was complete after 20 min. N-Acetyl-(S)-phenylalanine was isolated after workup in 97% yield and an optical purity of 99.6% ee.

EXAMPLE 5

Preparation of N-Acetyl-(S)-Cyclohexylalanine

110 μmol of the optically active diphenylphosphine ligand of Example 3 were dissolved in 5 ml of THF and, after addition of 100 μmol of $Rh(COD)_2BF_4$, stirred at RT for 20 min. 100 mmol of α-acetamidocinnamic acid and 250 ml of THF were added to the clear yellow solution. This solution was hydrogenated under 20 bar of hydrogen at 30° C. The reaction was complete after 20 min. The autoclave was then opened and air was passed in for 5 min to oxidize the phosphine ligand. After addition of 0.5 g of ruthenium oxide hydrate, a nuclear hydrogenation was carried out under 100 bar of hydrogen at 160° C. for 3 h. N-Acetyl-(S)-cyclohexylalanine was isolated in >95% yield with an ee of 99.6%.

We claim:

1. An optically active diphosphine ligand of the formula I

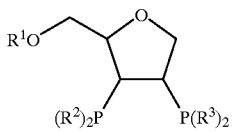

where:

$R^1$ is hydrogen, $C_1$–$C_{10}$-acyl, $C_1$–$C_{10}$-alkyl, $C_2$–$C_{10}$-alkenyl, each of which may be linear or branched, aryl, arylalkyl, in which the ring systems may be substituted in each case,

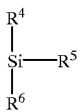

$R^2$, $R^3$ independently of one another are $C_1$–$C_{10}$-alkyl, which may be linear or branched, aryl, arylalkyl, in which the ring systems may be substituted in each case, $R^4$, $R^5$, $R^6$ independently of one another are $C_1$–$C_{10}$-alkyl, which may be linear or branched, aryl, arylalkyl, in which the ring systems may be substituted in each case, or its borane adduct.

2. An optically active diphosphine ligand of the formula Ia,

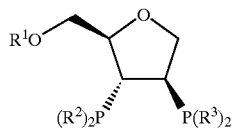

where the substituents have the meanings stated in claim 1, or its borane adduct.

3. A process for preparing optically active diphosphine ligands of the formula I as defined in claim 1, which comprises a) reacting an optically active α,β-unsaturated lactone of the formula II

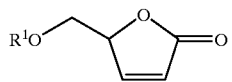

as Michael acceptor with the anion of $HP(R^2)_2$ and then with $HalP(R^3)_2$, where $R^1$ to $R^3$ have the meanings stated in claim 1, and b) reducing the carbonyl functionality of the diphosphine-substituted lactone of the formula III

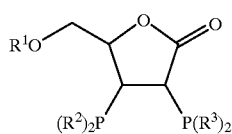

to the methylene group.

4. An optically active diphosphine ligand of the formula III

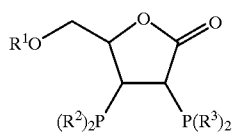

where the subsitutents have the meanings $R^1$ is hydrogen, $C_1$–$C_{10}$-acyl, $C_1$–$C_{10}$-alkyl, $C_2C_{10}$-alkenyl, each of which may be linear or branched, aryl arylalkyl, in which the ring systems may be substituted in each case,

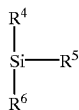

$R^2$, $R^3$ independently of one another are $C_1$–$C_{10}$-alkyl, which may be linear or branched, aryl, arylalkyl, in which the ring systems may be substituted in each case, $R^4$, $R^5$, $R^6$ independently of one another are $C_1$–$C_{10}$-alkyl, which may be linear or branched, aryl, arylalkyl, in which the ring systems may be substituted in each case, or its borane adduct.

5. A method for complexing metal compounds which comprises reacting the transition metal with an optically active ligand of the formula I as defined in claim 1.

6. A transition metal complex of the formula IV $$[M(L_n)(A)]^{p(+)} D^{q(-)} \quad \text{IV}$$

where:
- M is Co, Ir, Ni, Pd, Pt, Rh, Ru,
- A is an optically active diphosphine ligand of the formula as defined in claim 1,
- L is an olefinic ligand,
- D is the equivalent of a non-coordinated anion,
- n is 1 or 2,
- p, q are 0 to 4.

7. A process for preparing a transition metal complex as defined in claim 6, which comprises reacting an optically active diphosphine ligand of the formula I

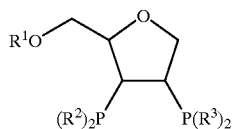

where
- $R^1$ is hydrogen, $C_1$–$C_{10}$-acyl, $C_1$–$C_{10}$-alkyl, $C_2$–$C_{10}$-alkenyl, each of which may be linear or branched, aryl arylalkyl, in which the ring systems may be substituted in each case,

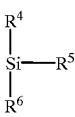

- $R^2$, $R^3$ independently of one another are $C_1$–$C_{10}$-alkyl, which may be linear or branched, aryl, arylalkyl, in which the ring systems may be substituted in each case,
- $R^4$, $R^5$, $R^6$ independently of one another are $C_1$–$C_{10}$-alkyl, which may be linear or branched, aryl, arylalkyl, in which the ring systems may be substituted in each case, or its borane adduct, in a manner known per se with a transition metal compound $(ML_n)^{p(+)} D^{q(-)}$, where the variables have the meanings stated in claim 6.

8. A method for the asymmetric hydrogenation of compounds with C—C, C—N and C—O multiple bonds which comprises carrying out the hydrogenation in the presence of a metal complex of the formula IV as defined in claim 6 as a catalyst.

9. A method for the asymmetric isomerization of allylamines to enamines which comprises carrying out the isomerization in the presence of a metal complex of the formula IV as defined in claim 1 as a catalyst.

* * * * *

UNITED STATES PATENT AND TRADEMARK OFFICE
CERTIFICATE OF CORRECTION

PATENT NO.: 5,990,320

DATED: November 23, 1999

INVENTOR(S): HELMCHEN et al.

It is certified that error appears in the above-identified patent and that said Letters Patent is hereby corrected as shown below:

Col. 9, claim 6, line 8, after "formula" insert --I--.

Signed and Sealed this

Twenty-fourth Day of April, 2001

Attest:

NICHOLAS P. GODICI

Attesting Officer

Acting Director of the United States Patent and Trademark Office